(12) United States Patent
Aramli

(10) Patent No.: US 10,660,451 B2
(45) Date of Patent: May 26, 2020

(54) BEDDING CLIMATE CONTROL APPARATUS AND METHOD TO OPERATE THEREOF THAT COMPENSATES FOR BACKPRESSURE AND AMBIENT TEMPERATURE

(71) Applicant: BEDJET LLC, Newport, RI (US)

(72) Inventor: Mark Darius Aramli, Newport, RI (US)

(73) Assignee: BEDJET LLC, Newport, RI (US)

( * ) Notice: Subject to any disclaimer, the term of this patent is extended or adjusted under 35 U.S.C. 154(b) by 0 days.

(21) Appl. No.: 16/372,372

(22) Filed: Apr. 1, 2019

(65) Prior Publication Data

US 2019/0223616 A1 Jul. 25, 2019

Related U.S. Application Data

(60) Division of application No. 15/681,998, filed on Aug. 21, 2017, now Pat. No. 10,524,581, which is a
(Continued)

(51) Int. Cl.
*A47C 21/04* (2006.01)
*A61F 7/00* (2006.01)
(Continued)

(52) U.S. Cl.
CPC ............ *A47C 21/044* (2013.01); *A47C 21/04* (2013.01); *A47C 21/042* (2013.01);
(Continued)

(58) Field of Classification Search
CPC ..... A47C 21/044; A47C 21/04; A47C 21/042;
A47C 21/048; A47G 9/0215; A47G 9/02;
A61F 7/00; F24F 11/80; F24F 11/74;
F24F 11/0008; F24F 11/58; F24F 11/59;
F24F 5/0096; F24F 5/00; F24F 13/24;
F24F 13/28; F24F 2013/242; F24F 2110/10;
(Continued)

(56) References Cited

U.S. PATENT DOCUMENTS 2,560,349 A * 7/1951 Inglis ................... A47C 21/044
392/383
3,230,556 A * 1/1966 Wiusor Shippee .. A47C 21/048
5/423
(Continued)

OTHER PUBLICATIONS

U.S. Appl. No. 15/681,998, filed Nov. 30, 2017, Aramil, claims.

*Primary Examiner* — Robert G Santos
*Assistant Examiner* — Rahib T Zaman
(74) *Attorney, Agent, or Firm* — Robert J. Hess; Hess Patent Law Firm (57) ABSTRACT

A bedding climate control apparatus that delivers, in a quiet manner, forced airflow from a fan/blower within a housing to selectively deliver tempered (heated via a thermal element) forced airflow and non-tempered (room temperature) forced airflow through a flexible air conduit to bedding. The thermal element imparts heat to temper the forced airflow and the heat deliver may be adjusted to maintain a constant set temperature by adjusting imparted heating power depending on backpressure changes in the forced airflow and ambient temperature.

16 Claims, 9 Drawing Sheets

Related U.S. Application Data continuation-in-part of application No. 15/441,217, filed on Feb. 23, 2017, now Pat. No. 9,907,407, application No. 15/441,217, filed on Feb. 23, 2017, now Pat. No. 9,907,407, which is a continuation-in-part of application No. 14/534,494, filed on Nov. 6, 2014, now Pat. No. 9,782,016, which is a continuation-in-part of application No. 29/501,656, filed on Sep. 5, 2014, now abandoned, which is a continuation-in-part of application No. 29/501,647, filed on Sep. 5, 2014, now Pat. No. Des. 733,269, which is a continuation-in-part of application No. 29/501,652, filed on Sep. 5, 2014, now Pat. No. Des. 750,858, which is a continuation-in-part of application No. 14/276,162, filed on May 13, 2014, now abandoned.

(60) Provisional application No. 61/966,042, filed on Nov. 6, 2013.

(51) Int. Cl.

| | | |
|---|---|---|
| *F24F 11/80* | (2018.01) | |
| *F24F 13/24* | (2006.01) | |
| *F24F 11/74* | (2018.01) | |
| *F24H 3/04* | (2006.01) | |
| *F24F 11/00* | (2018.01) | |
| *F24D 15/00* | (2006.01) | |
| *F24F 110/20* | (2018.01) | |
| *F24F 110/10* | (2018.01) | |
| *A47G 9/02* | (2006.01) | |
| *F24F 5/00* | (2006.01) | |
| *F24F 11/59* | (2018.01) | |
| *F24F 13/28* | (2006.01) | |
| *F24D 19/10* | (2006.01) | |
| *F24H 3/02* | (2006.01) | |
| *F24F 11/58* | (2018.01) | |

(52) U.S. Cl.
CPC .......... *A47C 21/048* (2013.01); *A47G 9/0215* (2013.01); *A61F 7/00* (2013.01); *F24D 15/00* (2013.01); *F24F 5/0096* (2013.01); *F24F 11/0008* (2013.01); *F24F 11/74* (2018.01); *F24F 11/80* (2018.01); *F24F 13/24* (2013.01); *F24H 3/0411* (2013.01); *A47G 9/02* (2013.01); *F24D 19/1096* (2013.01); *F24F 5/00* (2013.01); *F24F 11/58* (2018.01); *F24F 11/59* (2018.01); *F24F 13/28* (2013.01); *F24F 2013/242* (2013.01); *F24F 2110/10* (2018.01); *F24F 2110/20* (2018.01); *F24H 3/02* (2013.01)

(58) Field of Classification Search
CPC .. F24F 2110/20; F24D 15/00; F24D 19/1096; F24H 3/02; F24H 3/0411
See application file for complete search history.

(56) References Cited

U.S. PATENT DOCUMENTS

| | | | | |
|---|---|---|---|---|
| 3,444,922 A | * | 5/1969 | Dingman | A61H 35/00 165/247 |
| 4,660,388 A | * | 4/1987 | Greene, Jr. | A47G 9/0215 165/46 |
| 4,939,804 A | * | 7/1990 | Grant | A47C 21/044 5/423 |
| 4,959,877 A | * | 10/1990 | Covil | A47C 21/044 5/423 |
| 5,300,102 A | * | 4/1994 | Augustine | A47G 9/0215 165/46 |
| 5,324,320 A | * | 6/1994 | Augustine | A47G 9/0215 165/46 |
| 5,336,250 A | * | 8/1994 | Augustine | A47G 9/0215 5/423 |
| 5,405,371 A | * | 4/1995 | Augustine | A47G 9/0215 607/107 |
| 5,578,230 A | * | 11/1996 | Eldon | A47G 9/0215 219/211 |
| 5,730,120 A | * | 3/1998 | Yonkers, Jr. | A47C 21/044 128/202.13 |
| 6,473,920 B2 | * | 11/2002 | Augustine | A61F 7/00 5/421 |
| 6,698,046 B1 | * | 3/2004 | Wu | A47C 27/082 137/625.15 |
| 6,701,552 B2 | * | 3/2004 | Suzuki | A47C 21/048 5/421 |
| 7,036,163 B2 | * | 5/2006 | Schmid | A47C 21/044 5/421 |
| 7,631,377 B1 | * | 12/2009 | Sanford | A47C 21/044 5/413 R |
| 7,913,332 B1 | * | 3/2011 | Barnhart | A47C 21/044 5/423 |
| 8,332,975 B2 | * | 12/2012 | Brykalski | A47C 21/044 5/421 |
| 8,353,069 B1 | * | 1/2013 | Miller | A47C 21/048 5/421 |
| 9,192,244 B2 | * | 11/2015 | Rand | A47C 21/044 |
| 2002/0100121 A1 | * | 8/2002 | Kocurek | A47G 9/0215 5/482 |
| 2003/0036786 A1 | * | 2/2003 | Duren | A47C 21/04 607/96 |
| 2003/0140418 A1 | * | 7/2003 | Klamm | A47C 21/022 5/423 |
| 2004/0253920 A1 | * | 12/2004 | Schoettle | A47C 21/044 454/338 |
| 2006/0085911 A1 | * | 4/2006 | Tompkins | A47C 21/048 5/423 |
| 2006/0137099 A1 | * | 6/2006 | Feher | A47C 7/74 5/713 |
| 2008/0028533 A1 | * | 2/2008 | Stacy | A61G 7/015 5/713 |
| 2008/0308106 A1 | * | 12/2008 | Augustine | A47C 7/744 128/205.29 |
| 2010/0101418 A1 | * | 4/2010 | Augustine | A47C 21/044 95/273 |
| 2011/0289664 A1 | | 12/2011 | Parish | |
| 2011/0289684 A1 | * | 12/2011 | Parish | A47C 21/044 5/421 |
| 2013/0036549 A1 | * | 2/2013 | McKlarney | A47C 21/044 5/413 R |
| 2017/0340128 A1 | | 11/2017 | Aramli | |

* cited by examiner

BEDDING CLIMATE CONTROL APPARATUS AND METHOD TO OPERATE THEREOF THAT COMPENSATES FOR BACKPRESSURE AND AMBIENT TEMPERATURE

CROSS-REFERENCE TO COPENDING PATENT APPLICATIONS

This patent application is a division of
(1) U.S. utility application Ser. No. 15/681,998 filed Aug. 21, 2017 and entitled "BEDDING CLIMATE CONTROL APPARATUS AND METHOD OF OPERATING SAME", which is a continuation-in-part of
(2) U.S. utility patent application Ser. No. 14/534,494 filed Nov. 6, 2014 and entitled "BEDDING CLIMATE CONTROL APPARATUS WITH FORCED AIRFLOW FOR HEATING AND VENTILATING", which in turn asserts a benefit of invention priority from the filing of
(3) U.S. provisional patent application No. 61/966,042 filed Nov. 6, 2013 and entitled "Forced air thermal device for a bed with integrated wireless RF remote controls and optional wi-fi/Bluetooth controls" and is a continuation-in-part of each of:
(4) U.S. design patent application Ser. No. 29/501,652 filed Sep. 5, 2014 entitled "AIR DELIVERY OUTLET NOZZLE" that matured into U.S. D750858 S on Mar. 1, 2016;
(5) U.S. design patent application Ser. No. 29/501,656 filed Sep. 5, 2014 and entitled "HOUSING FOR A CLIMATE CONTROL APPARATUS"; and
(6) U.S. design patent application Ser. No. 29/501,647 filed Sep. 5, 2014 and entitled "SLEEVED HOSE" that matured into U.S. D733,269 S on Jun. 30, 2015;
(7) U.S. utility patent application Ser. No. 15/441,217 filed Feb. 23, 2017 and entitled "Blanket Apparatus for Distributing Conditioned Air Into Zones of a Bed", published under publication no. 2017-0164758 A1, which is a continuation-in-part of U.S. utility patent application Ser. No. 14/276,162 filed May 13, 2014 now abandoned.

INCORPORATION BY REFERENCE TO COPENDING PATENT APPLICATIONS

This patent application incorporates subject matter by reference to copending patent applications of the same inventor as that of the present application:
(1) U.S. utility patent application Ser. No. 14/534,494 filed Nov. 6, 2014 and entitled "BEDDING CLIMATE CONTROL APPARATUS WITH FORCED AIRFLOW FOR HEATING AND VENTILATING"
(2) U.S. provisional patent application No. 61/966,042 filed Nov. 6, 2013 and entitled "Forced air thermal device for a bed with integrated wireless RF remote controls and optional wi-fi/Bluetooth controls";
(3) U.S. design patent no. US D750858 S that issued on Mar. 1, 2016;
(4) U.S. design patent application Ser. No. 29/501,656 filed Sep. 5, 2014 and entitled "HOUSING FOR A CLIMATE CONTROL APPARATUS", now abandoned;
(5) U.S. design patent no. US D733269 S that issued on Jun. 30, 2015; and
(6) U.S. utility patent application Ser. No. 15/441,217 filed Feb. 23, 2017 and entitled "Blanket Apparatus for Distributing Conditioned Air Into Zones of a Bed", which is published under publication no. 2017-0164758 A1.

BACKGROUND OF THE INVENTION

Technical Field of the Invention

The invention is a home appliance that provides very rapid heating of a bed via forced heated air prior to the user entering the bed, or while the user is in the bed and also provides a cooling effect after the user has entered the bed via fresh room temperature air being forced into the bedding. That is, the invention relates to supplying forced air, which may be heated, within a space between a fitted mattress sheet and a bedding sheet or within a layer of bedding. Further, a wireless protocol access device is used to send commands remotely to the bedding climate control apparatus that affect operating parameters of the apparatus and includes setting the temperature of a space between a fitted mattress sheet and a bed sheet by delivery of forced air, which may be heated with heating power as warranted.

Description of Related Art

Current control of the temperature of a bed relies on electric blankets or electric mattress pads. These devices are limited in their wattage capability and typically take 30 to 45 minutes to raise the temperature of bedding by 20 degrees F. As well, they provide no means to cool the user. They also provide no circulation of fresh air into the bedding.

Some products are currently in use in the medical field that provide forced air bed heating to patients in surgical recovery rooms. These devices cannot be used without proprietary gowns with airflow channels or perforated sheets with airflow channels that must be connected to the forced air heater for distribution of the heat to the patient. These products are also not used for cooling.

The Electric Blanket Institute finds that the average electric blanket puts out less than 200 watts of heating power, and some portion of this energy is emitted to the topside of the blanket into the bedroom.

Electric blankets have embedded wires, which one can feel and these wires can be chewed on by pets or damaged by children and sharp objects.

Many electric blankets aren't reliable after repeated washings or have very special washing and drying instructions that must be followed. The present inventor has found by observing through an IR camera that wires of a brand new blanket purchased from a major department store after 45 minutes on "Hi" setting do not provide even heating. Older electric blankets cause hundreds of fires a year from wires in the bed.

It is desired to deliver heat to bedding and sheets or to provide the sensation of cooling to a person within the bedding and sheets, all under direction from a bedside remote control. In so doing, it is desired to deliver to bedding and sheets more dry heating power than is available from electric blankets in a safe and quiet manner at a temperature that is the same as provided by a household HVAC central air-heating unit, and forced ambient temperature air in a controllable fashion

SUMMARY OF THE INVENTION

The present invention pertains to a method and means of operation of a bedding climate control apparatus.

That is, In response to wireless receipt of commands by a bedding climate control apparatus of the present invention, the bedding climate control apparatus varies a temperature or humidity of a space between a bed sheet and a fitted mattress sheet or within a layer of bedding in accordance with the commands. Preferably, the bedding climate control apparatus is responsive to simultaneous and non-simultaneous receipt of commands from both a protocol access enabled device and a remote control wireless communication device to vary, in accordance with the commands, the temperature or humidity within a space between a bed sheet and a fitted mattress sheet or within a layer of bedding.

The operation of the bedding climate control apparatus may be equipped with appropriate means to perform the following steps or functions:

receiving commands with a signal receiver of the bedding climate control apparatus;

sensing the temperature or humidity of the space between bedding and a fitted mattress sheet;

transmitting in a wireless manner feedback such as the sensed temperature or humidity of the space to a location that is beyond confines of the bedding climate control apparatus.

delivering forced air into the space in accordance with the commands so as to give rise to an inflated configuration of the space bounded by the bed sheet and the fitted mattress sheet or bounded within a layer of bedding imparting thermal energy to the forced airflow with a thermal element in accordance with the commands; and operating at least one device to remotely receive the information from the bedding climate control apparatus and to send out in a wireless manner the commands.

The bedding climate control apparatus is preferably responsive to receipt of the commands to carry out a course of action in accord with the commands, the course of action being selected from the group consisting of commencement of adjustment in a temperature or humidity, setting a change in temperature or humidity as a function of time over a time interval, and carrying out operation of the bedding climate control apparatus in a manner that conforms with recall settings from memory storage that are selected from the group consisting of time, temperature, humidity and air flow rate.

There is preferably a method of adjusting temperature or humidity within bedding, comprising the steps of:

equipping a bedding climate control apparatus with components including a thermal element that imparts thermal energy to vary a temperature or a humidity in a bed before that of an environment surrounding the bed;

operating at least one device in wireless communication with the bedding climate control apparatus to transmit simultaneous and non-simultaneous commands in a wireless manner, the at least one device being selected from the group consisting of a protocol access enabled device and a remote control wireless communication device, the protocol access enabled device being selected from the group consisting of Bluetooth protocol access enabled, WiFi protocol access enabled and Zigbee protocol access enabled; and operating the equipped bedding climate control apparatus to receive the transmitted simultaneous and non-simultaneous commands from both the protocol access enabled device and the remote control wireless communication device to have the components vary the temperature or humidity in the bed in a manner that is in accord with the commands.

The bedding climate control apparatus is not a room air conditioning system, which adjusts the temperature or humidity of a whole room even if that room happens to have a bed in it. Room air conditioning systems do eventually change the temperature or humidity of a bed within the room eventually since the bed is within the room, but the environment surrounding the bed has its temperature or humidity changed by the room air conditioning system before that of the bed. The reverse is the case for a bedding climate control apparatus in accordance with the invention since the components of the apparatus, including the thermal elements, adjust the temperature or humidity of the space between a bed sheet and a fitted sheet initially without affecting the surrounding environment at that initial time. After a while, there may be some localized lead through effect on the immediately surrounding environment that changes the temperature or humidity of that immediately surrounding environment since the bedding is made of fabric that can breathe, but that arises well after the temperature or humidity of the space has begun to change.

An aspect of the invention reside in a bedding climate control apparatus that delivers, in a quiet manner, forced airflow from a fan/blower within a housing to selectively deliver tempered (heated via a ceramic thermal element) and untempered (room temperature) air through an air duct to bedding. The quiet manner is attained by oversizing a size of the housing to accommodate acoustic foam, oversizing a dimension of the fan/blower, oversizing a heating capacity of the thermal element, and oversizing a dimension of the flexible hose beyond the size actually needed for efficient operation.

The capacity of the housing is oversized beyond that needed to accommodate just the fan/blower so that it can accommodate acoustic foam at the air intake to dampen sound generation by the fan/blower. The acoustic foam is arranged so there is no direct line of sight between the air supply and the air intake to the fan/blower, thereby forcing air entering the fan/blower to have previously deflected off the acoustic foam to thereby dampen its sound.

The capacity of the fan/blower to deliver needed airflow exceeds that necessary for attaining the desired airflow. As a result, the fan/blower is run at quieter speeds than would be the case if it were sized to efficiently deliver the needed airflow. One reason for being able to run the motor of the fan/blower at a lower speed is that the pressure drop that the airflow must overcome to reach the bedding is kept low.

In furtherance of this goal, a ceramic thermal element, which is used to heat or temper the air flow, is oversized so its capacity exceeds that necessary for the heat delivery needed. As a result, the oversized thermal element can heat more of the airflow at a time (than can a smaller dimensioned ceramic thermal element) to have the airflow reach a lower temperature than would be the case if it were smaller in dimension. This lower temperature is below the flashpoint of dust and lint, which thus do not burn when subjected to heat from the ceramic thermal element operating at the lower temperature delivery. If the ceramic thermal element were sized smaller it would need to operate to deliver the heat at a higher temperature in order the handle the air flow requirements for tempered airflow.

The air duct is oversized to lessen the pressure drop across it for the required airflow and thus avoid the need to run the motor of the fan/blower at a higher speed to overcome the pressure drop, which would be the case is the air duct were sized smaller to be suited to handle the full air flow volume.

A further aspect is to sense air temperature of the airflow emerging from a discharge of the blower/fan and from an air delivery outlet so as to vary a temperature of the forced air being delivered to bedding as necessary to maintain substantially a constant temperature throughout a time interval, as well as to shut off heating power in the event that the airflow temperature is to high as to risk reaching burn temperature.

Another aspect is to vary a setting of the temperature of the forced air being delivered to bedding as time passes. Still another aspect is to deliver the force air to bedding initially at a maximum temperature setting for a relatively short duration such as ten minutes to provide maximum heating and to automatically thereafter change the temperature setting to a lower temperature for a relatively longer duration (such as overnight). Yet another aspect resides in controlling the bedding climate control apparatus with a wireless remote control unit and with a blue-tooth protocol access enabled wireless smart phone at the same time or at different times. The control may include commencement of forced airflow, heating of the forced airflow, setting a change in temperature of the heated forced airflow as a function of time over a time interval, recall time, temperature and air flow rate settings from memory storage, setting an alarm to automatically turn on and off the bedding climate control apparatus at specific times. The smart phone may work in conjunction with a software application retrieved from the internet to interact with the bedding climate control apparatus.

Still another aspect resides in delivering heating power at a level that prevents tripping a conventional electrical circuit of a household and in preventing high heat delivery from potentially burning skin of a person under certain conditions by delivering between 1000 watts of heating power to a maximum of 1500 watts of heating power inclusive and heating the forced air to a maximum set temperature substantially at 46 degrees Celsius maximum or below (114 degrees Fahrenheit).

An additional aspect resides in a longitudinally expandable/compressible flexible hose that keeps its interior air passage dimension intact even when longitudinally compressed and flexed to bend. The longitudinally expandable/compressible flexible hose has a steel wire wound inside to maintain the air passage dimension intact. The entire flexible hose may be sheathed within a stretchable manmade fabric such as spandex, or non-stretchable material.

Another aspect resides in the fan/blower being operated with a DC brushless motor that enables 0-100% adjustability in motor power so that airflow from the fan/blower powered by the motor permits airflow adjustment increments of as small as 5%. Thus, a user could adjust the airflow delivery volume to any of 20 settings at 5% increments from 0 to 100%. Certainly, 10 settings at 10% increments could be done instead if desired within the range of 0 to 100% power. That would still be preferable to the limited three choices available conventionally for blowers of just low, medium or high.

A further aspect resides in a bed sheet retention unit that has clamps that clamp onto a bed sheet to keep its position over the air delivery outlet nozzle. This helps to ensure that airflow will enter the space between the upper sheet and lower fitted mattress sheet regardless of how the occupant of the bed might move them during sleep. Since there are platform beds that have a raised lip about their periphery, the bed sheet retention unit has two horizontally disposed segments jointed to each other by a vertically disposed segment (riser), which rises to an elevation that is higher than the peripheral wall of the conventional partition bed. As an alternative, the air conduit may provide the retention function by providing the clamps at the end of the air conduit.

Preferably, the housing of the bedding climate control apparatus should be sized to fit beneath conventional beds and thus be up to seven inches in height. Therefore the bedding climate control apparatus sits next to or under the foot of the bed and sends forced hot or cool air in between the bedding top sheet and bottom fitted mattress sheet via the air delivery outlet nozzle, which is small and unobtrusive and is anchored at the bottom corner of the bed.

Once activated, the blower/fan, flexible hose and air delivery outlet nozzle operate at a very specific air pressure to quietly generate a small cushion of turbulent air between the upper bedding sheet and lower fitted mattress sheet that lifts the top bedding sheet off the fitted mattress sheet by a few inches. This tenting effect on the bedding combined with the airflow that follows enables the bedding climate control apparatus air to permeate throughout the entire sleeping area and provide even heating or cooling. Alternatively the forced air may be blown in between layers of bedding, or into layers of bedding containing hollow flow cavities in accord with U.S. utility patent application publication no. 2017-0164758 A1

For heating, the bedding climate control apparatus is operated to heat three to five minutes before getting into bed to achieve a 30 degrees F. bedding pre-heat, or for short bursts while already in bed. For cooling, turn the climate control apparatus on while in bed. It is quiet, the bedding climate control apparatus emits much less noise than a room air conditioner.

Another aspect resides in a grille within the exhaust air passage of the/blower/fan that prevents fingers from reaching through the exhaust air passage live electrical components within the fan/blower despite the dimension of the exhaust air passage being large enough in dimension to enable fingers to fit in. This relatively larger size exhaust air passage means that the fan/blower can deliver the necessary volume of airflow with a lesser pressure drop through the air duct than would otherwise be the case if sized smaller.

BRIEF DESCRIPTION OF THE DRAWING

For a better understanding of the present invention, reference is made to the following description and accompanying drawings, while the scope of the invention is set forth in the appended claims.

DETAILED DESCRIPTION OF THE INVENTION

Figure 1:
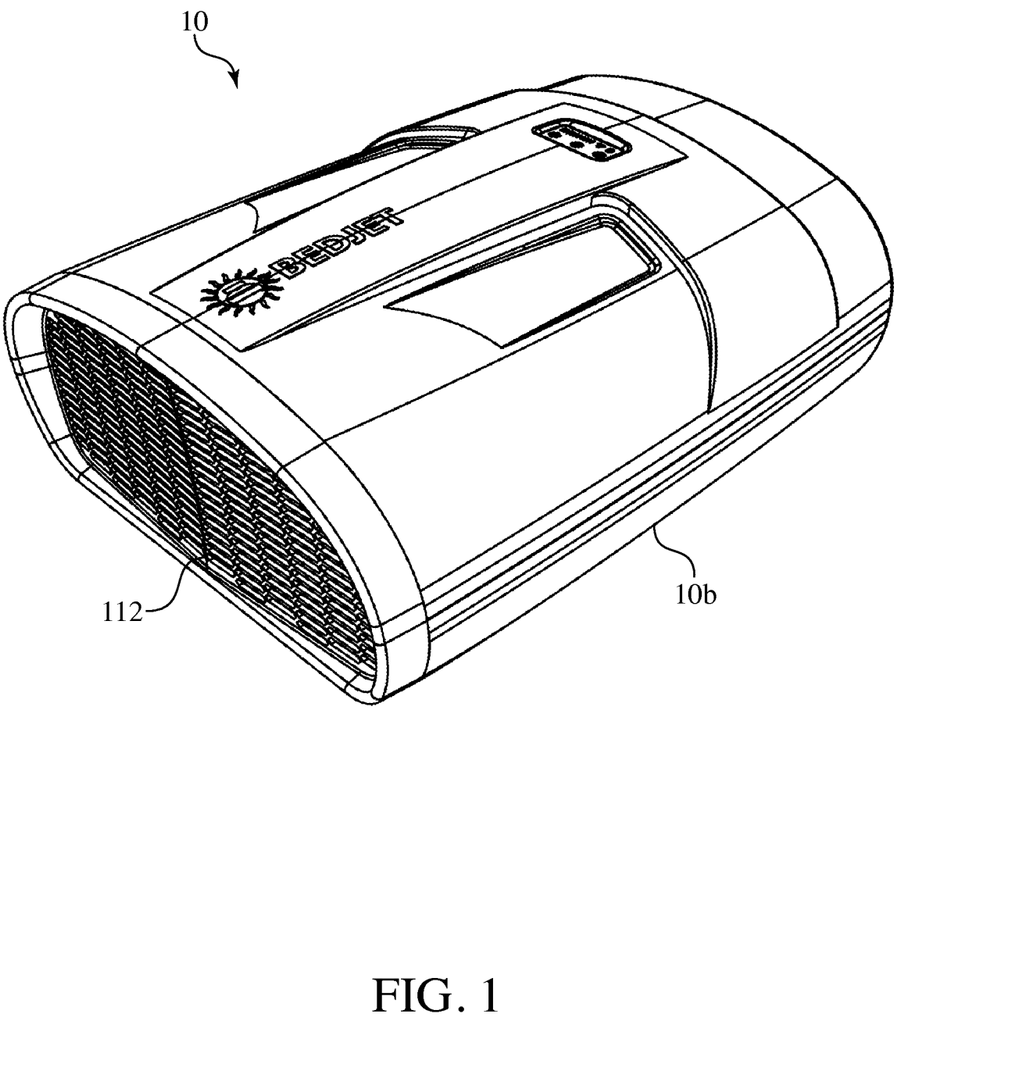
FIG. 1 is an isometric view of the bedding climate control apparatus of the invention.

Turning to the drawing, FIG. 1 shows a bedding climate control apparatus 10 is shown in accordance with the invention. The bedding climate control apparatus 10 has housing 106 that contains a fan or blower (not shown in FIG. 1) that receives air via air intake grille 112. The air may be tempered or heated with a thermal element (not shown in FIG. 1) that is contained within the housing 106 in the discharge side of the fan or blower. The structure of the housing 106 corresponds to that depicted in U.S. design patent application Ser. No. 29/501,656, whose contents are incorporated herein by reference.

Figure 2:
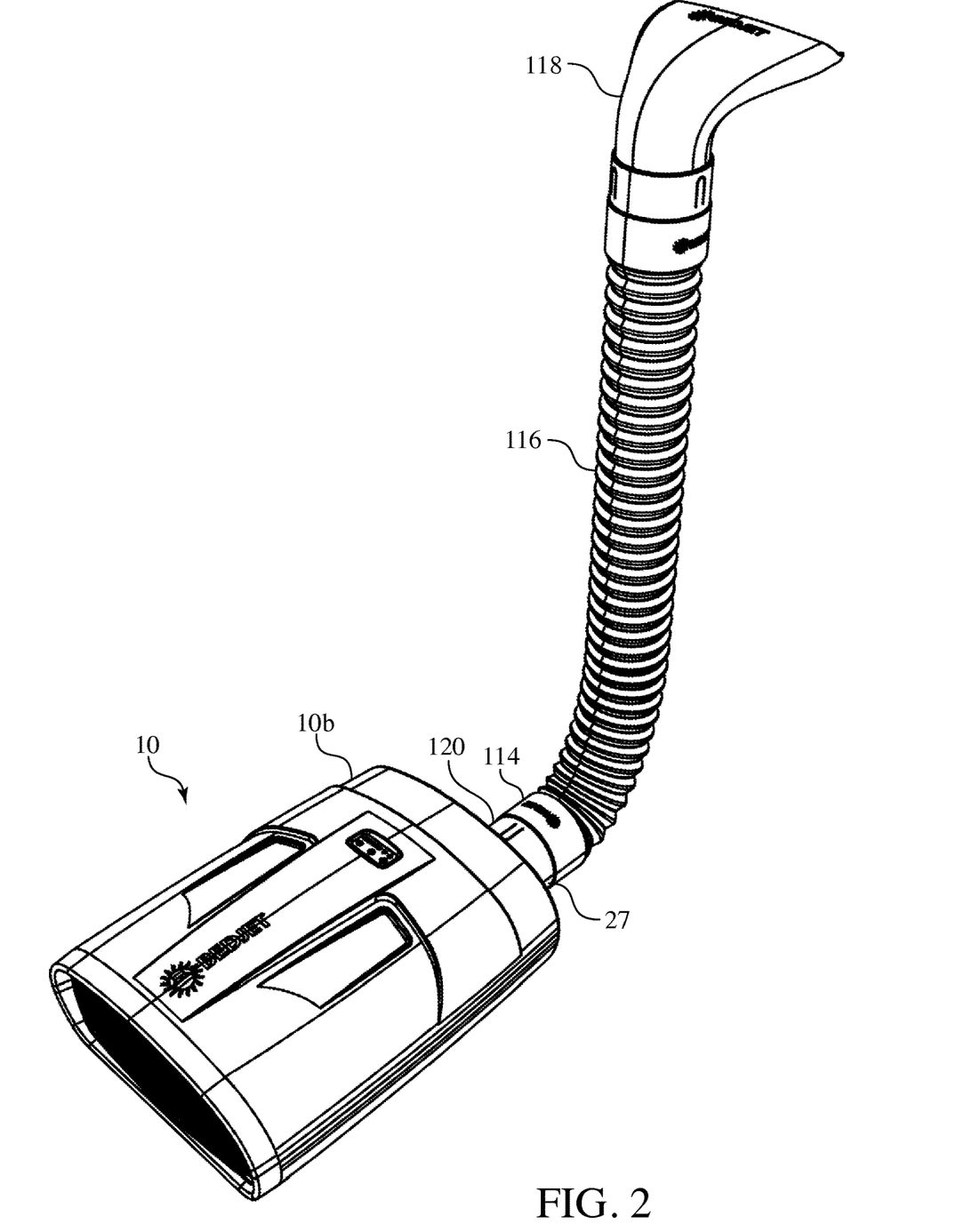
FIG. 2 is an isometric view of an assembly of an air delivery outlet nozzle secured to a distal end of a longitudinally compressible/expandable hose, whose proximal end is secured to a discharge port of the bedding climate control apparatus of FIG. 1.

FIG. 2 shows the bedding climate control apparatus 10 of FIG. 1. Air enters through the intake grille 112 and exits through the cylindrical discharge outlet 120. An end 114 of a hose 116 is mechanically coupled to the cylindrical outlet 120 of the bedding climate control apparatus 10 via any conventional mechanical coupler 27, such as engaging screw threads (not shown). The hose 116 is hollow and serves as an air duct. The distal end of the hose 116 is connected to an inlet opening of an air delivery outlet nozzle 118 through which discharges airflow.

Figure 3:
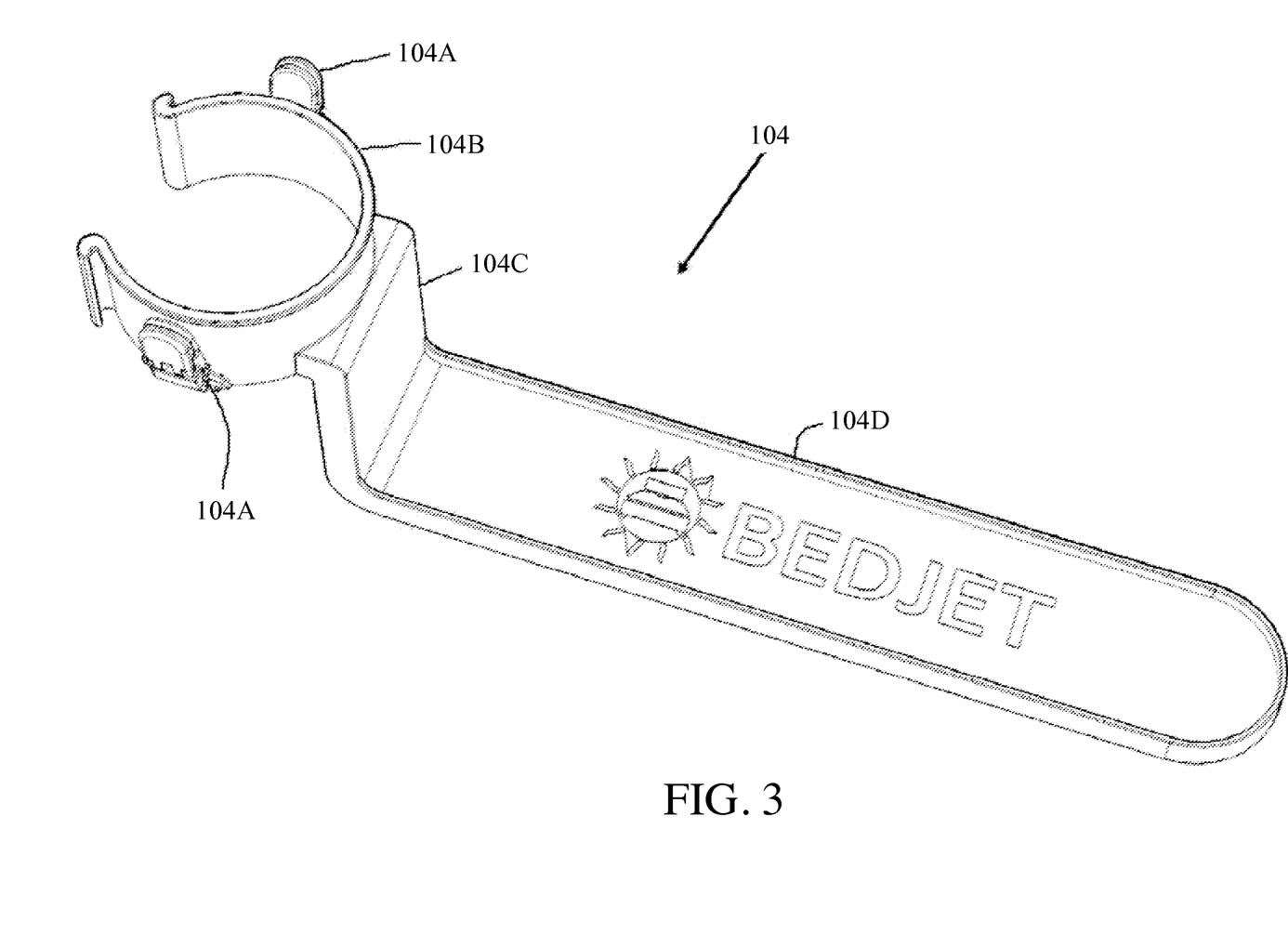
FIG. 3 is an isometric view of the bed sheet retention unit in accordance with the invention.

The hose 116 may be sheathed by a spandex fabric as depicted in US design patent application Ser. No. 29/501,647, whose contents are incorporated herein by reference. The hose 116 is preferably longitudinally compressible and longitudinally expandable to enable it to bend and yet maintain the dimension of its interior. An embedded steel wire wraps around the length of the hose 116 in a spiral manner that resists radial compression or expansion and thus retains the interior dimension regardless of the bending of the hose 116. For instance, the hose 116 may be bent 180 degrees and the interior dimension remains substantially unchanged. By contrast, a smooth walled hose without such an embedded, spiral wound metal wire feature would collapse on the bend or have a reduced/constricted flow path, There are a number of ways different hoses can achieve outer diameter support—nearly all involve some type of reinforcement in the outer walls, whether it be ribs, grooves, spiral wound wire, or exceptionally thick outer walls (even these will collapse if the bend is enough), FIG. 3 shows a bedding sheet retention unit 104 that has means for clamping a bed sheet, namely, two clamps 104A diametrically opposite each other on a horizontally extending grasping portion that also includes means for holding the flexible hose 116, namely, a horizontally extending open ring-shaped segment 104B. The flexible hose 116 of FIG. 2 will fit within the internal opening defined by the ring-shaped segment 104B. There is a vertically extending riser segment 104C that rises vertically between an end of a horizontally extending base segment or paddle 104D and the ring-shaped segment 104B.

The open ring-shaped segment 104B may be closed to grasp about a periphery of the hose to prevent horizontal movement of the flexible hose 116. If the ring-shaped segment 104 is corrugated on its inward facing side, the corrugations are sized to enter grooves on the exterior of the flexible hose 116 to retain the flexible hose 116 in position against relative vertical movement where the retention takes place.

The horizontally extending base segment or paddle 104D is elongated and will lie beneath a mattress and provides firm support for the performance of the retaining and holding functions. The vertically extending riser segment 104C extends along an end of the mattress at the foot of a bed. The vertically extending riser segment 104C may be height adjustable by being formed of two sliding elements that slide relative to each other vertically and secured in any relative position with respect to each other in any conventional manner that two sliding pieces may be retained in their relative position with respect to each other, such as with a series of holes in one of the sliding pieces and a spring-loaded button in the other that enters into one of the series of holes when aligned and can be urged manually against spring bias to leave the hole to free the sliding pieces from their relative position.

Figure 4:
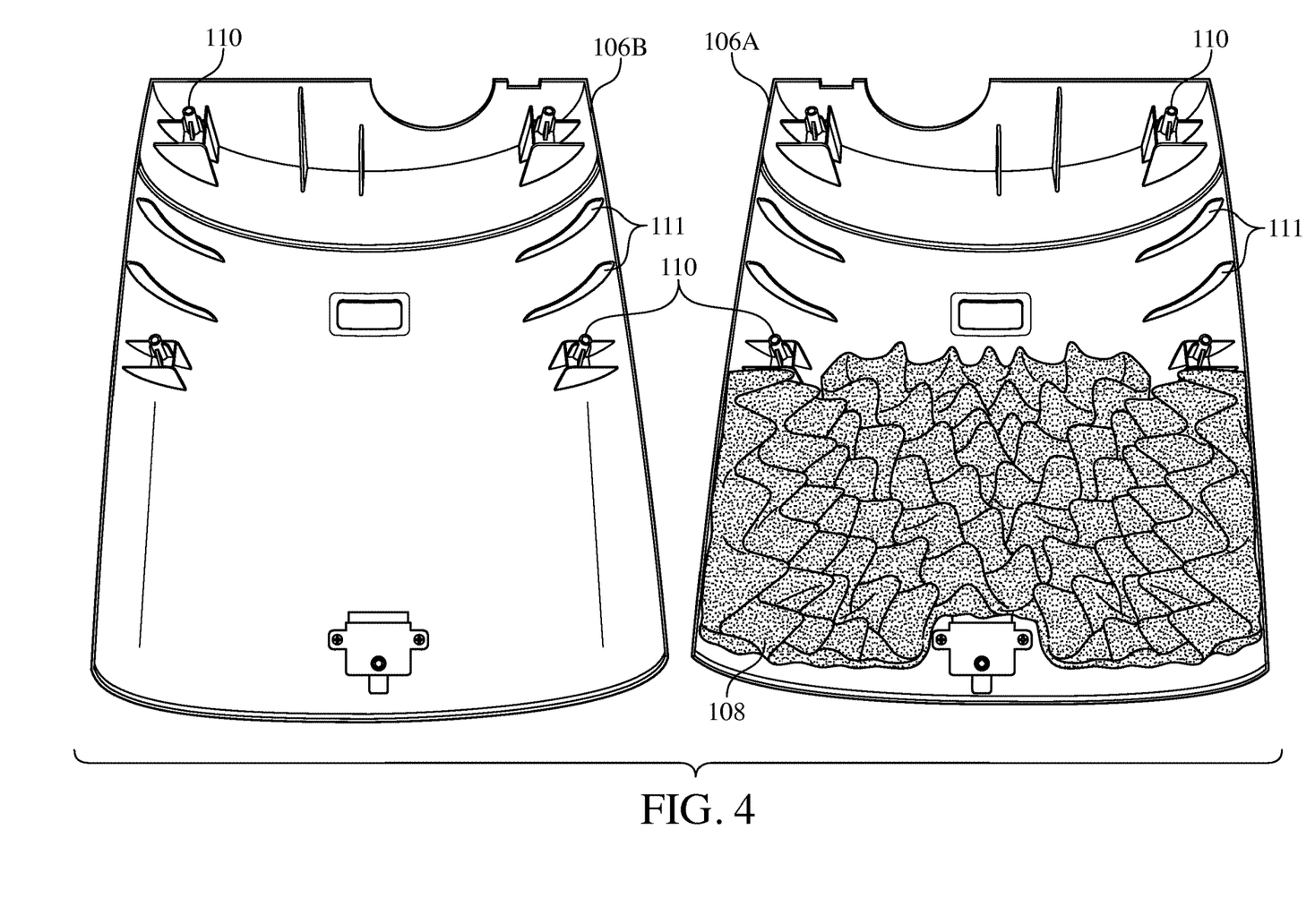
FIG. 4 is an isometric view of the housing of FIG. 1 opened to show the acoustic foil assembled in position in accordance with the invention.

FIG. 4 shows two shell halves 106A, 106B of a housing 106 with one of the two shell halves 106A accommodating acoustic foam 108 in a secure manner within about one half of the interior side of the one of the two shell halves 106A that is closer to the grille 112 (FIG. 1). Thus, air entering the grille 112 strikes the acoustic foam 108 (FIG. 4) and thus there is a dampening effect on the noise otherwise generated from the airflow. It will be understood that the two shell halves 106A, 106B may be secured to each other in any conventional manner, such as via aligned screw threaded fastening elements 110 into which a screw stem is threaded with its head recessed. The two shell halves 106A, 106B may each have supporting ribs 111 to help strengthen them. Instead of foam 108, other kinds of dampening materials may be used such as some fibrous non-woven materials or various cloths. Noise reduction is also possible with the use of a deflector that doesn't require any type of absorbent to realized desired noise reduction. Such a deflector may be a physical shield in which the airflow needs to travel through a path in which there is no direct line of sight from the intake of the blower to the air supply, i.e., via a tortuous path.

Figure 5:
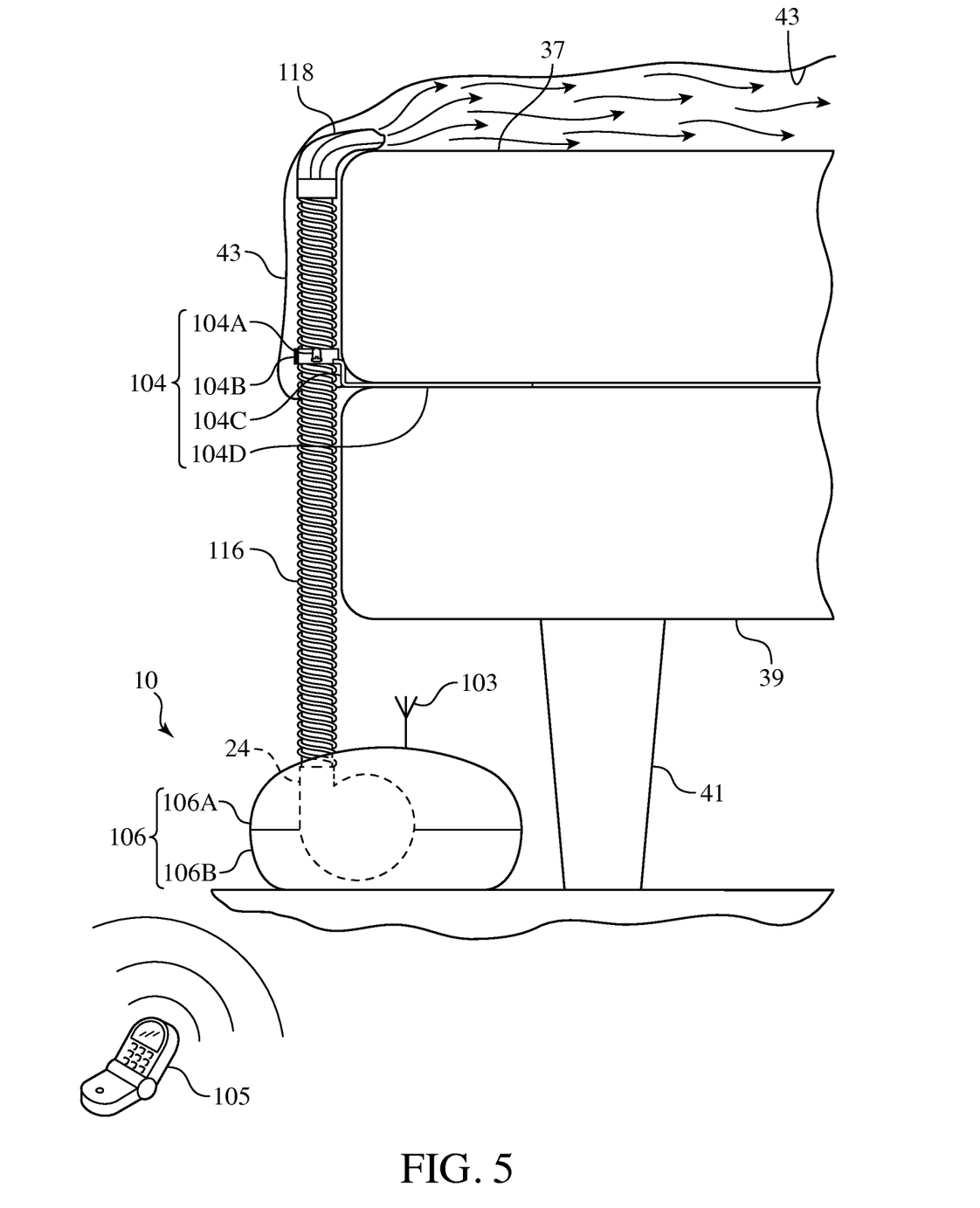
FIG. 5 is a schematic view of the assembly of FIG. 2 and the bed sheet retention unit of FIG. 3 clamped to sheets for a conventional bed having a box spring and mattress.

FIG. 5 shows the bedding climate control apparatus 10 on a floor beneath a bed to blow forced air through the hose 116 and out the air delivery outlet nozzle 118 to enter space between a fitted mattress sheet covered mattress 37 and a bed sheet 43 that overlays the fitted mattress sheet. As a result of this delivery of forced air into the space, the space inflates to increase the volume of the space and thus give rise to an inflated configuration of the bed sheet as shown in FIG. 5. The fitted mattress sheet covers the top, both sides, both ends and a portion of the underside of the mattress by opposite ends of the mattress, The bed is partially shown, with its fitted mattress sheet covered mattress 37 atop a box spring 39 elevated by a frame leg 41. The hose 116 extends from the fan/blower discharge in the bedding climate control apparatus to rise to the air delivery outlet nozzle 118 at the foot of the bed. The bedding retention unit 104 (see FIG. 3) has its horizontally extending base segment or paddle 104D between the mattress 37 and the box spring 39 so as to be against the underside of the mattress 37 and against the topside of the box spring 39 as shown in FIG. 5. The vertically extending riser segment 104C elevates the horizontally extending open ring-shaped segment 104B. The two clamps 104A are clamped to the bed sheet 43. The hose 116 is retained by the horizontally extending open ring-shaped segment 104B.

Figure 6:
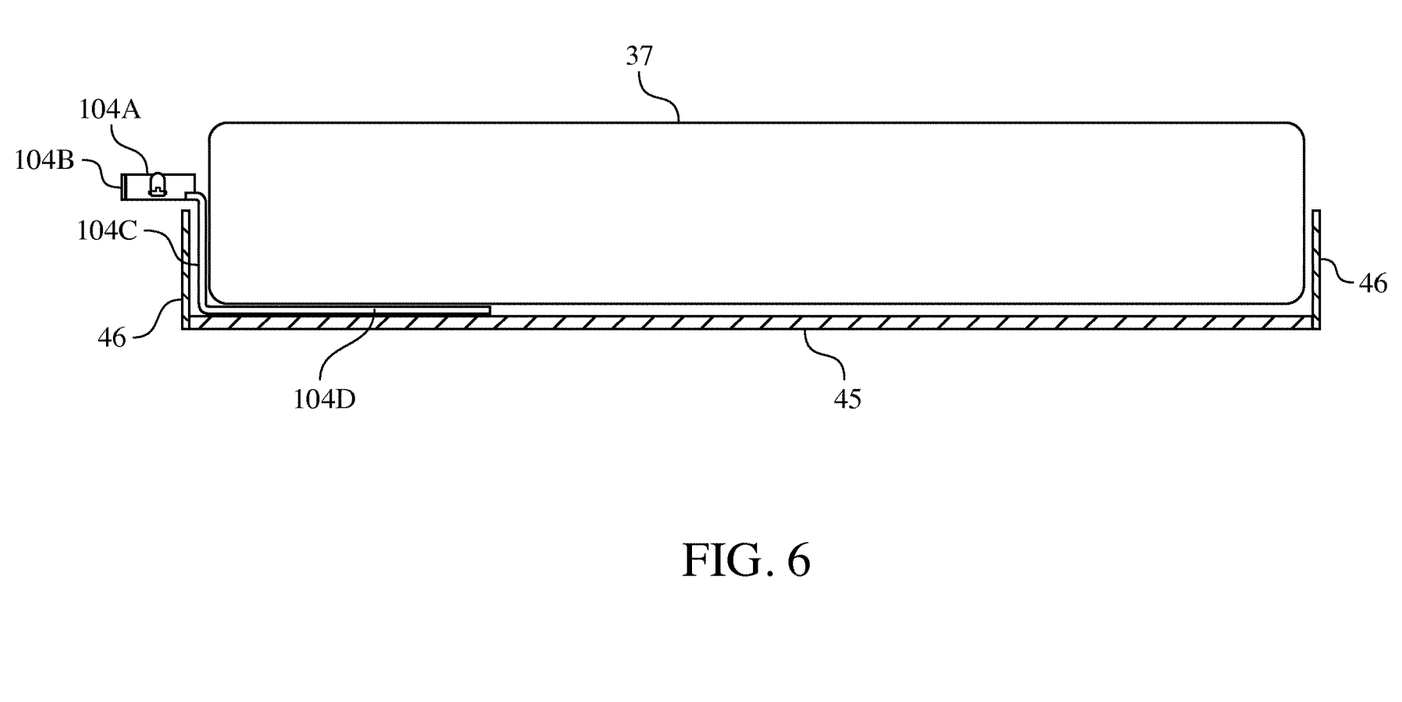
FIG. 6 is a schematic view of the assembly of FIG. 2 with the bed sheet retention unit of FIG. 3 clamped to sheets for a conventional partition bed.

FIG. 6 shows a partial view of a platform bed 45 used in place of the box spring 39 and frame leg 41 of FIG. 5. The fitted mattress sheet covered mattress 37 rests on a base of the platform bed 45 so that the bedding retention unit 104 is positioned in a like manner except that the horizontally extending base segment or paddle 104D lies between the underside of the fitted mattress sheet covered mattress 37 and the topside of the base of the platform bed 45 so as to be against both as shown in FIG. 6. Some platform beds have a peripheral lip 46 that extends upward about the periphery of the base. The vertically extending riser segment 104C elevates the horizontally extending ring-shaped segment 1048 to an elevation higher than the top of the lip 46 region of the horizontally extending open ring-shaped segment 104B that meets the top of the vertically extending riser segment 104C clears the lip 46.

Figure 7:
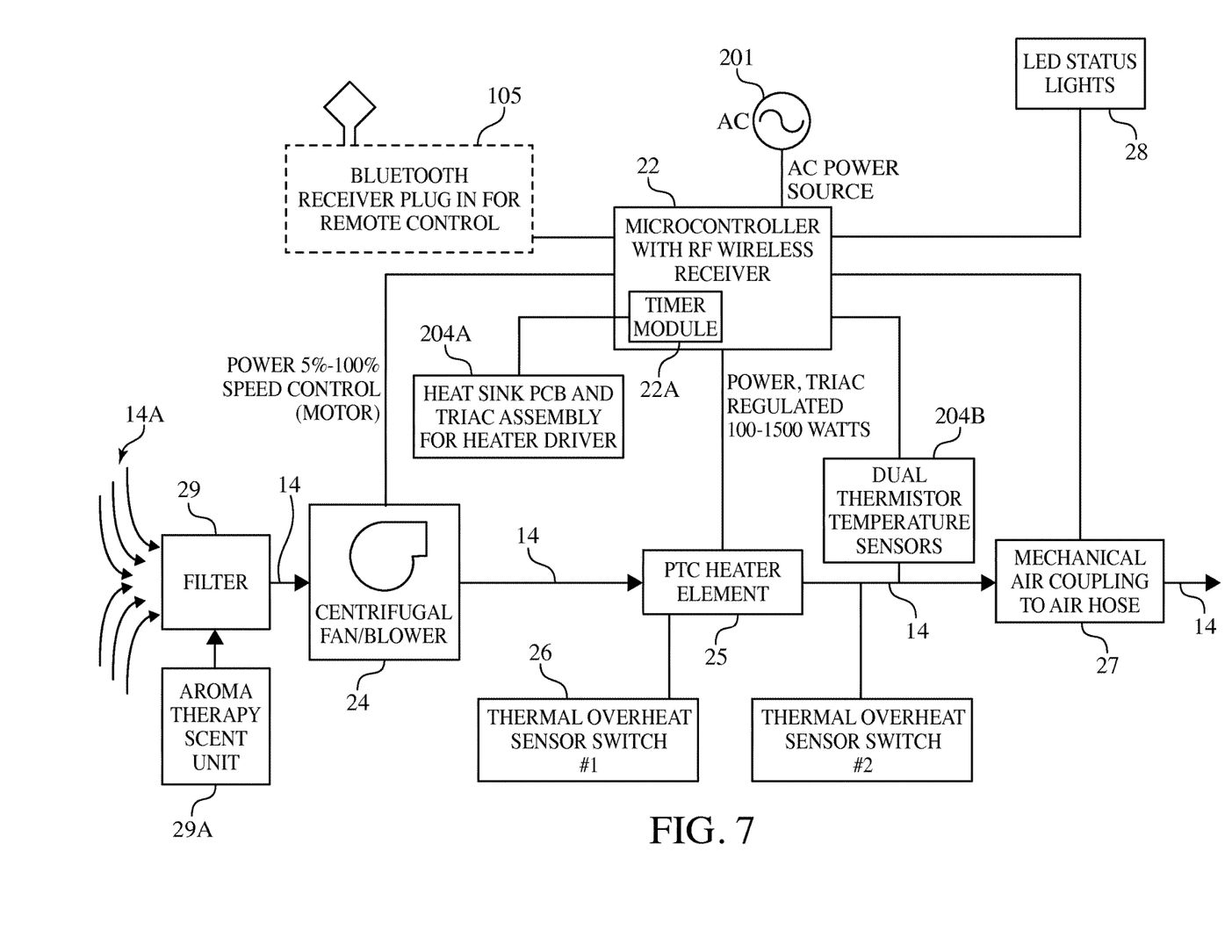
FIG. 7 is a functional block diagram of the bedding climate control apparatus of FIG. 1 and wireless connectivity.

FIG. 7 is a functional block diagram that shows the operative components of the assembly of FIG. 2 and wireless connectivity. A conventional air filter 29 is provided whose purpose is to remove particulates such as dust, lint, pollen, mold and bacteria from the ambient air source 14A. A suitable air filter 29 is a high-efficiency particulate absorption (HEPA).

An aroma therapy optional scent unit 29A, which may be an aromatherapy device, may be provided to administer aroma or scents into the airflow to provide scented or aromatic air that mixes with the filtered air from the filter 29.

The centrifugal fan/blower 24 is operated to suck in filtered airflow 14 from the air source 14A so as to increase the speed of the filtered airflow 14 through the centrifugal fan/blower 24 to a constant volume flow rate by rotating impellers that cause acceleration of the air radially and a change in the direction of the airflow.

A ceramic PTC heater element 25 heats the filtered airflow as it emerges from the centrifugal fan/blower 24 The thermal element may be a 1500 watt positive temperature coefficient (PTC) heater element 25 using Nichrome wire or ceramic thermal elements sized to 13 Amperes power consumption.

An overheat condition may arise in theory from blockage of the air delivery outlet nozzle 118 if the airflow is left unchecked or from equipment malfunction. This is a reason for detecting the airflow temperature with dual thermistor temperature sensors 204A so that if the temperature gets too close to reaching a burn temperature (an unacceptable overheat condition), a thermal overheat sensor switch 26 triggers to shut off power to the PTC heater element 25.

That is, the response of the thermal overheat sensor switch 26 to a sensing that the overheat condition is imminent is to disrupt the main AC power to thwart the overheat condition from being realized. The thermal overheat sensor switch 26 would be triggered to disrupt the main AC power well in advance of the air temperature actually reaching the burn temperature yet higher than the constant air temperature that the bedding climate control apparatus seeks to maintain.

There is a need to disperse built-up body heat and moisture with a dry and refreshing room temperature breeze in between the sheets and over one's body. Such is readily accomplished with the bedding climate control apparatus 10 by blowing forced air between the top sheet and fitted mattress sheet via the hose with the air delivery outlet nozzle with the forced air (unheated by the ceramic thermal element 25). That is, the ceramic thermal element 25 is shut off so as to avoid heating the air passing through.

A microcontroller 22, which is powered by an AC power source 201, controls the fan/blower 24, PTC heater element 25 in accordance with manual controls or remote signals transmitted by a protocol access enabled remote device 105 such as Bluetooth or WiFi or Zigbee (and/or wireless remote controller) and received via a signal receiver 103, which conveys the received signal to the microcontroller 22 that decodes the received signal. The microcontroller 22 also receives temperature information of the airflow from the dual thermister temperature sensors 204B that sense the temperature of the airflow leaving the centrifugal blower/fan 24. There could be a temperature sensor located at the air delivery outlet nozzle to detect localized high temperature should such arise to trigger another thermal overheat sensor switch 26 to cut off power to the PTC heater element 25.

The heat sink PCB (printed circuit board) and TRIAC assembly 204A serves as the heater driver to drive the heater element 25. A variac has one primary coil and one secondary coil, and the number of 'effective' turns on the secondary is varied by means of a sliding contact that 'taps' the secondary coil along its length. By this means, one can control the output voltage in tiny steps, each equivalent to one turn. The heat sink PCB and triac assembly 204A responds to command signals from the microcontroller 22 to vary the output voltage to drive the PTC heater 25 accordingly to heat at a particular temperature set in accord with the microcontroller 22. The microcontroller 22 issues the appropriate command signals to the heat sink PCB and triac assembly 204A corresponding to the particular temperature based upon inputs from the Bluetooth protocol access enabled remote device 105 and/or wireless remote controller and/or the airflow temperature information sensed by the dual thermister temperature sensors 204B.

The microcontroller 22 sends commands to illuminate LED lights 28 to signify the status of operation, including temperature, error code, on/off status. The microcontroller 22 has logic and circuitry necessary for reaching and maintaining a steady or substantially constant airflow temperature for the airflow provided by the fan/blower 24.

The microcontroller 22 includes a timer module 22A that may be set to any suitable time for heating the volume of air, such as changing the temperature setting hourly to a different temperature for heating purposes.

A unique feature of the invention is the ability to raise the temperature of the bedding/sheets of a king or queen sized bed by 20 degrees F. in less than 5 minutes. This temperature rise gives the user the feeling from the bedding of a "hot towel just out of the dryer" when entering the bed, which provides comfort and delight to the user. It provides heating to more than 75% of the sleeping surface area of king or queen size bedding (including both lower and upper extremity of the user) with a just a very small (less than 8") protrusion into the bottom of the bed by the air delivery outlet nozzle.

Another feature of the invention is supplying room temperature forced air into the bedding (which is at lower temperature than interior of the bedding due to natural human body heat) and thus the person in the bed experiences a sensation of cooling from the forced air.

The invention has special electronics and relays enabling user on/off control and heating/cooling control via a wireless radio frequency remote control. The wireless remote feature combined with the bed heating invention is considered a key unique element of the function of the system and its useability in its application. The invention is intended to be a pre-heater for cold winter beds, raising the temperature of the bed over a period of several minutes before the user enters the bed (although it can be used while the user in the bed). As such the wireless remote enables to user to activate the invention from other parts of the home while preparing for bed, enabling full pre-heat time.

The invention includes a housing, a high pressure variable speed fan/blower/with brushless AC motor, an electric thermal element, special control electronics and a flexible air output hose or duct with unique air delivery outlet nozzle. The invention housing is located near but not in or attached to the bed and a bed sheet retention unit is inserted into the bottom of bed in between the mattress and the bedding (i.e., the user sleeping layer).

Some of the main features of the invention include:

raising the temperature of the bedding/sheets of a king or queen sized bed by 20 degrees F. in less than 5 minutes to give the user the feeling from the bedding of a "hot towel just out of the dryer" when entering the bed, which provides comfort and delight to the user.

supplying hot air at less than 135 degrees F. to prevent skin burns. Skin burns are prevented by appropriately regulating the airflow and/or the temper of the airflow and/or duration of tempered airflow. For instance, the response upon sensing that the airflow temperature entering the bedding space is too close to skin burn temperature, commands are issued to reduce or shut off power accordingly. That is, the power to the high-pressure variable blower fan to lessen or stop the forded airflow and/or the power to the thermal elements to lessen or stop their tempering of the forced airflow. The duration of the reduction or shutoff may also be regulated through the issuance of appropriate commands.

operating a user adjustable auto-shutoff timer that will shut the unit down after between 3 and 10 minutes of operation.

protecting against reaching burn temperature with thermal over-temperature shut off safety.

utilizing the maximum amount of intermittent current allowed from typical 15 amp household bedroom electrical circuit yet sized to enable maximum speed in heating of bedding.

utilizing Nichrome wire or ceramic thermal elements sized at to 13 Amps power consumption.

using several user adjustable heat settings, as well as adjustable air flow settings enabling activation of the unit from a distance separated by several rooms in a house with remove RF wireless controls enabling activation of the unit from smart phones and tablet computers with optional Wi-Fi Bluetooth controls.

heating to more than 75% of the sleeping surface area of king or queen size bedding (including both lower and upper extremity of the user) with a just a very small (less than 8") protrusion into the bottom of the bed of the air delivery outlet duct/flange.

The invention's forced air approach uses a high-pressure variable blower/fan that delivers between 40 to 100 CFM of air flow at minimum 0.3" $H_2O$ static pressure, and up to 1" $H_2O$ static pressure without stalling. The flow rate is variable by user knob setting to accommodate for different bed sizes and bedding types. This very specific flow rate and static pressure has been determined to be the key element necessary to enable the invention to provide even heating to 75% of the bedding surface area of a king or queen size bed with just a small air outlet duct protrusion into the bottom of the bed.

Using this very specific airflow rate and static pressure delivery range, a tenting effect of the top layer of bedding above the mattress is created. 75% or more of the top layer of bedding covering the mattress surface area is lifted from the mattress by several inches via a cushion of air. This cushion of air layer created in between the bedding and mattress enables the turbulent warm air from the invention to freely distribute the heat throughout the bedding surface area. The unique flow rate and static pressure is also a key element for using normal bedding that may become irregularly bunched up or not be smoothly laid on the bed (i.e, a perfectly made bed).

The invention has electronics and relays enabling user on/off control and heating/cooling control via a wireless radio frequency remote control. The wireless remote feature combined with the bed heating invention is considered a key unique element of the function of the system and its useability in its application. The invention is intended to be pre-heater for cold winter beds, raising the temperature of the bed over a period of several minutes before the user enters the bed (although it can be used while the user in the bed). As such, the wireless remote enables to user to activate the invention from other parts of the home while preparing for bed, enabling full pre-heat time.

The electronics and relays may enable user on/off control and heating/cooling control via wireless Wi-Fi protocol connection or Bluetooth protocol connection or Zigbee protocol connection, thus enabling smart phone or tablet computers to be utilized as the remote control.

In furtherance of this, the temperature of the forced airflow into the inflated, tented space (between the bed sheet and the fitted mattress sheet) is sensed and transmitted out from the bedding climate control apparatus. The remote control (such as a Bluetooth/Wi-Fi/Zigbee protocol access enabled controller) may be equipped to receive the transmitted sensed temperature over time and undertake an analysis. The analysis may determine that a desired temperature has been reached in which case instructions are transmitted from the remote control to the bedding climate control apparatus to stop the forced airflow. The bedding climate control apparatus is responsive to those instructions to do just that, i.e., shut off the forced airflow. The remote control may be equipped with a display to depict a result of the analysis, such as a graphical representation of a change in the temperature of the inflated, tented space over time.

In addition, the remote control may be programmed or receive instructions from an application that is accessible from the Internet or wireless network to send commands to the bedding climate control apparatus in accordance with settings that were initiated by the user of the remote control. For instance, an increment shut off timer may be set by the user through the programming or via the application accessible on the Internet to provide appropriate settings as to how the bedding climate control apparatus is to attain changes in temperature incrementally over time and shut off the forced airflow as those incremental temperatures are reached over time. The increment shut of timer, whether in the programming or in the application accessible on the Internet, triggers the remote control to send appropriate instructions to the bedding climate control apparatus to carry out the settings over time as they apply. The bedding climate control apparatus responds accordingly by either altering the heating power delivered to the forced airflow or altering a speed of the forced airflow (such as to zero for shutoff or higher or lower that affects the amount of time it will take to reach a desired incremental temperature.

For example, in cooling mode, if the user wanted the temperature of the space to change gradually or rapidly, the speed of the airflow delivery could be varied accordingly to accommodate. On the other hand, in heating mode, if the user wanted the temperature of the space to change gradually or rapidly, then, in addition to varying the speed of the airflow delivery or even to avoid the need to vary the airflow delivery speed, the amount of heat power delivered to the airflow could be varied.

Indeed, the forced airflow may be shut down entirely for a particular period of time after a desired temperature for the inflated, tented space has been reached and resumed as warranted.

Therefore, as shown in FIGS. 5 and 7, the invention pertains to a method of operation of a bedding climate control apparatus, comprising the steps of receiving commands with a signal receiver 103 of the bedding climate control apparatus 10 that affect operating parameters of the bedding climate control apparatus 10 and set a desired temperature;

Inflating a space between a fitted mattress sheet and a bed sheet into an inflated configuration by delivery into the space of forced airflow from a centrifugal fan/blower 24, hose 116, and air delivery outlet nozzle 116 (each of the bedding climate control apparatus);

changing the temperature of the inflated space over time to reach the at least one desired temperature by effecting the delivery of the forced airflow into the space subsequent to attaining the inflated configuration and, as warranted, imparting heating power with a thermal element or PTC heater element 25 to the forced airflow all in accordance with the received commands;

sensing with dual thermistor temperature sensors 204B the temperature realized as a result of the changing;

ceasing, under direction from a microcontroller 22, the delivery of the forced airflow from a centrifugal fan/blower 24 after the sensed temperature reaches the desired temperature; and transmitting feedback such as in the form of the sensed temperature as information sent out from the bedding climate control apparatus. That is, devising the feedback pertains to a condition of the space (e.g., the condition is the temperature of the space after adjustment), which arises as a result of the implementation of the operation of the bedding climate control apparatus. The signal receiver 103 may also have signal transmitting capability to serve as a signal transmitter as well.

The invention as shown in FIGS. 5 and 7 also pertains to a bedding climate control apparatus, comprising means 103 for receiving commands with a bedding climate control apparatus 10 that affect operating parameters of the bedding climate control apparatus 10 and identifying at least one desired temperature;

means for inflating a space between a fitted mattress sheet and a bed sheet into an inflated configuration by delivery into the space of forced airflow from a centrifugal fan/blower 24, hose 116, and air delivery outlet nozzle 116 (each of the bedding climate control apparatus);

means for changing a temperature of the inflated space over time to reach the at least one desired temperature by effecting delivery of the forced airflow into the space subsequent to attaining the inflated configuration and, as warranted, imparting heating power (PRC heater element 25) to the forced airflow all in accordance with the received commands;

means for sensing (dual thermistor temperature sensors 204B) the temperature of the inflated space that is realized as a result from the means for changing the temperature;

means (microcontroller 22) for ceasing the delivery of the forced airflow from a centrifugal fan/blower 24 after the sensed temperature reaches the desired temperature; and means for transmitting feedback such as the sensed temperature as information sent out from the bedding climate control apparatus. The signal receiver 103 may also have signal transmitting capability to serve as a signal transmitter as well.

If desired, a spandex fabric sleeve may sheath the hose 116 of FIG. 2 to soften the appearance at bends of the hose since the bends of the hose are in a compressed state. Such a compressed state arises from the hose being in a bent condition, will be concealed by the fabric sleeve, which takes on a generally cylindrical shape with the hose extending within the confines of the fabric sleeve.

Figure 8:
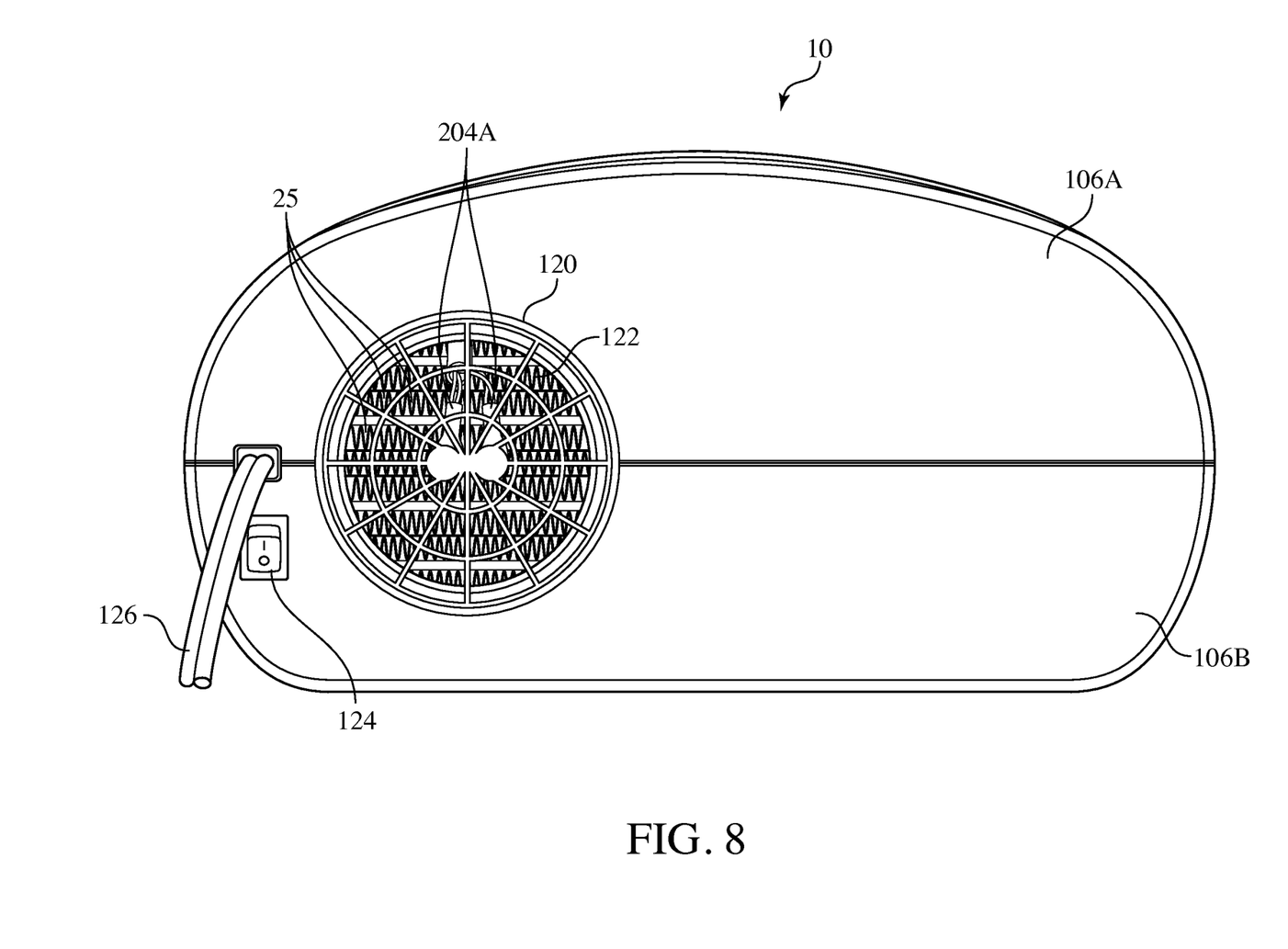
FIG. 8 is an end view of the bedding climate control apparatus housing of the discharge side.

FIG. 8 shows the discharge side of the upper and lower housing 106A, 106B of the bedding climate control apparatus 10. An outlet metal grille guard 122 is within the confines of a projecting cylindrical discharge outlet 120 through which airflow from the fan exits to enter the hose 116 of FIG. 2. The outlet metal grille guard 122 blocks a person's fingers from entering the interior of the housing of the bedding climate control apparatus 10. A manually operated mechanical on-off switch 124 is accessible for turning on or off the bedding climate control apparatus 10, although not shown in FIG. 7. A power cord 116 conveys AC power to the bedding climate control apparatus 10. The manually operated mechanical on-off switch functions to turn on or off power to run the centrifugal blower/fan 24 and PTC heater element 25 of FIG. 7. The dual thermistor temperature sensors 204B of FIG. 7 may be attached to the outlet metal grille 122 to detect the exiting airflow temperature at the outlet metal grille 122.

Figure 9:
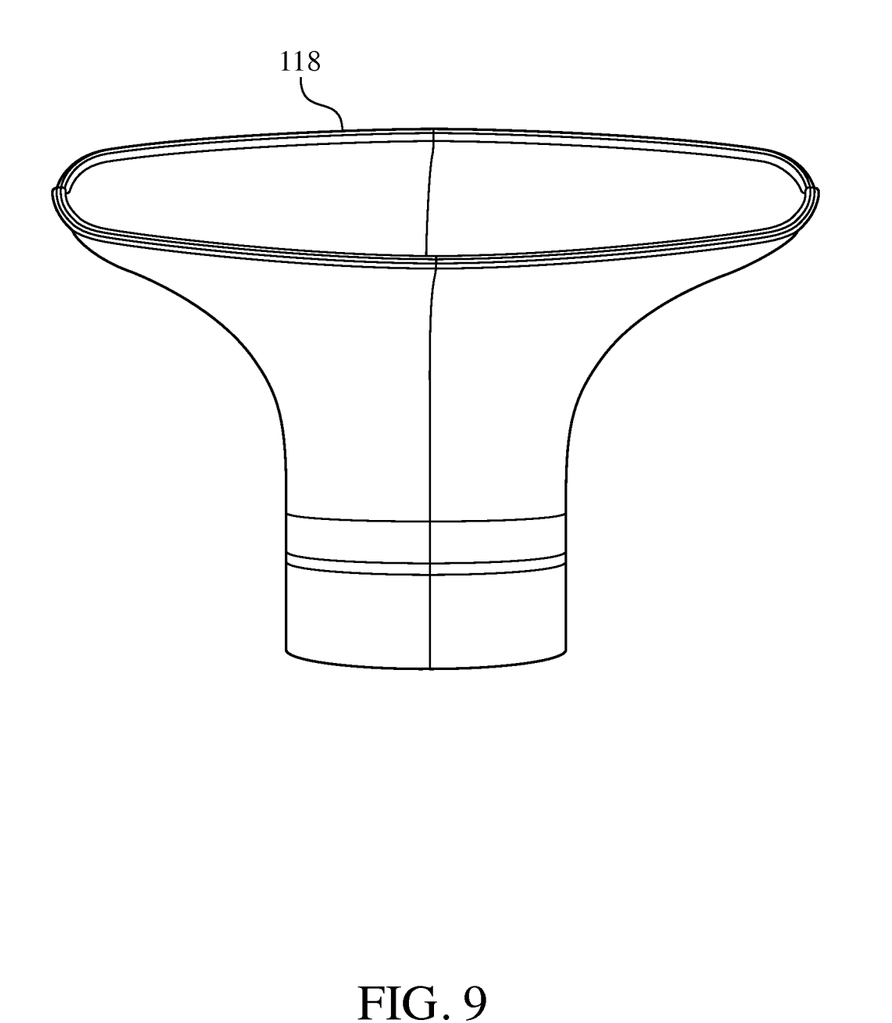
FIG. 9 is an isometric view of the air delivery outlet nozzle in accordance with the invention.

FIG. 9 shows the air delivery outlet nozzle 118 of FIGS. 2 and 5, which is hollow. The structure of the air delivery outlet nozzle 118 corresponds to that depicted in US design patent application Ser. No. 29/501,652, whose contents are incorporated herein by reference.

In the inflated configuration, the space receiving the forced air has a periphery bounded by the bed sheet and the fitted mattress sheet. By forcing air into the space via the air delivery outlet nozzle 118, the region of the space that is away from the periphery (e.g, in more of a central region) realizes an adjustment in its temperature or humidify before that of the periphery. In that sense, the forced air delivery reaches the central region of the space faster than conventional approaches that rely on radiative elements or hot or cold fluid tubes to heat or cool the space since they are arranged about the periphery of the space and thus adjust the temperature at the periphery of the space before the central region of the space is affected.

Nevertheless, the present invention as it relates to receiving commands in a wireless manner and transmitting feedback in a wireless manner is not necessarily limited to bedding climate control apparatus that utilize forced air to adjust the temperature of the space between a bed sheet and a fitted mattress sheet. Such a receipt of commands (to act in accord with) and the transmission of feedback (such as the temperature or humidity condition) may be utilized for other kinds forms of heat transfer including conduction, diffusion, convection and radiation. For instance, tubes may be within the mattress that contain a fluid that is either heated or chilled. A blanket may be used that contains radiative heating elements. These may be utilized individually or in combination with each other or with the forced air convection of the preferred embodiment and each may be controlled using the wireless manner of the present invention for receiving commands to implement the heat transfer effect and for transmitting feedback of the sensed heat transfer effect or other pertinent criteria to evaluate the effectiveness of the implementation of the heat transfer effect.

Some examples of how the bedding control apparatus may operate include operating the thermal element to adjust power to maintain a constant set temperature that would be either user set or pre-preprogrammed. The heating power of the thermal element would adjust depending on backpressure changes in the airflow and ambient temperature to maintain the set temperature. The operating may be in a mode where first a heating power is delivered and then automatically after any time a lesser heating power is delivered or, with automatic time shutoff activated, no heating power is delivered at all. If desired, the thermal element may be operated at a certain power and then switched to power off while the fan is still running (for cooling using ambient temperature), Preferably, the operating of the thermal element is such that it is activated or deactivated at a certain preset dock time and operating of the blower or fan (with no heating power from the thermal element) is effected such that it is activated or deactivated at a certain preset clock time or other user programmed "event".

While the foregoing description and drawings represent the preferred embodiments of the present invention, various changes and modifications may be made without departing from the scope of the present invention.

What is claimed is:

1. A method of operation of a bedding climate control apparatus, comprising the step of:
    operating a bedding climate control device by:
    actuating a blower or a fan to discharge forced airflow into an air conduit;
    conditioning the forced airflow to reach set parameter values;
    delivering the conditioned, forced airflow via the air conduit into a space within bedding to inflate same;
    sensing a parameter of the conditioned, forced airflow to provide readings of the sensed parameter;
    compensating, based on the readings, for changes in the conditioned, forced airflow attributed to backpressure change in the conditioned, forced airflow and to ambient temperature change by further conditioning the conditioned, forced airflow to again reach the set parameter values, and
    creating a tenting effect of a top layer of the bedding by varying a flow rate of the forced airflow within a range of between 40 to 100 cubic feet per minute inclusive at a static pressure within a range of between 0.3 inch of water to 1 inch of water inclusive so as to lift 75% or more of the top layer of the top layer of the bedding via a cushion of air that enables a turbulent airflow to freely distribute the forced airflow throughout a surface area of the bedding surface area, regardless of whether the bedding is smoothly laid or whether the bedding is irregularly bunched up.

2. The method of claim 1, wherein the further conditioning includes imparting heating power via a thermal element to the forced airflow.

3. The method of claim 1, wherein the further conditioning includes humidifying the forced airflow.

4. The method of claim 1, wherein the further conditioning includes ventilating with the forced airflow.

5. The method of claim 1, wherein the further conditioning includes ventilating, heating and humidifying the forced airflow.

6. The method of claim 1, further comprising: retaining an interior hollow dimension of the air conduit substantially intact even as the air conduit bends or lengthens.

7. The method of claim 1, further comprising: changing a speed of the conditioned, forced airflow; and in response to the changing of the speed, changing an amount of heat imparted via a thermal element into the forced airflow accordingly to compensate for the change in the speed.

8. A method of operation of a bedding climate control apparatus, comprising:
    the step of operating a bedding climate control device by:
    actuating a blower or a fan to discharge forced airflow into an air conduit;
    conditioning the forced airflow to reach set parameter values;
    delivering the conditioned, forced airflow via the air conduit into a space within bedding to inflate same;
    sensing a parameter of the conditioned, forced airflow to provide readings of the sensed parameter; and
    compensating, based on the readings, for changes in the conditioned, forced airflow attributed to backpressure change in the conditioned, forced airflow and to ambient temperature change by further conditioning the conditioned, forced airflow to again reach the set parameter values,
        wherein the conditioning of the forced airflow includes heating the forced airflow with a thermal element that is oversized beyond that necessary to heat the forced airflow to reach the set parameter wherein the set parameter is a set temperature.

9. A method of operation of a bedding climate control apparatus, comprising:
    the step of operating a bedding climate control device by:
    actuating a blower or a fan to discharge forced airflow into an air conduit;
    conditioning the forced airflow to reach set parameter values;
    delivering the conditioned, forced airflow via the air conduit into a space within bedding to inflate same;
    sensing a parameter of the conditioned, forced airflow to provide readings of the sensed parameter;
    compensating, based on the readings, for changes in the conditioned, forced airflow attributed to backpressure change in the conditioned, forced airflow and to ambient temperature change by further conditioning the conditioned, forced airflow to again reach the set parameter values; and
    configuring the bedding climate control device so that the forced airflow overcomes a pressure drop from passing through the air conduit to reach the space in the bedding and oversizing each of the blower or the fan and the air conduit to exceed respective dimensions necessary to enable delivery of the forced airflow at the set parameter to the space so that the pressure drop is lower than otherwise and so that the noise level generated from operation of the blower or the fan is maintained at less than 65 decibels at one meter away.

10. The method of claim 1, further comprising:
    issuing commands with each of a wireless controller and a wireless protocol access enabled device, the bedding climate control device being responsive to receipt of the commands from both the wireless controller and the wireless protocol access enabled device at the same time to commence operation of the bedding climate control apparatus in accordance with the commands.

11. The method of claim 1, further comprising: issuing commands with each of a wireless controller and a wireless protocol access enabled device, the bedding climate control device being responsive to receipt of the commands to retrieve recall settings from memory storage in accord with the commands and carrying out operation of the bedding climate control apparatus in accord with the retrieved recall settings, the recall settings being selected from the group consisting of time of commencement of the airflow, duration of the airflow, cessation of the airflow, temperature of the airflow, flow rate of the airflow and any combination thereof.

12. The method of claim 2, further comprising:
shutting off the thermal element and the blower or the fan each in accord with different time intervals from different settings for each with an auto-shutoff timer.

13. A bedding climate control apparatus, comprising: a bedding climate control device configured to operate by: actuating a blower or a fan to discharge the forced airflow into an air conduit; conditioning the forced airflow to reach set parameter values; delivering the conditioned, forced airflow via the air conduit into a space within bedding to inflate same; sensing a parameter of the conditioned, forced airflow to provide readings of the sensed parameter; compensating, based on the readings, for changes in the conditioned, forced airflow attributed to backpressure change in the conditioned, forced airflow and to ambient temperature change by further conditioning the conditioned, forced airflow to again reach the set parameter values, wherein the bedding climate control device is configured to create a tenting effect of a top layer of the bedding by varying a flow rate of the forced airflow within a range of between 40 to 100 cubic feet per minute inclusive at a static pressure within a range of between 0.3 inch of water to 1 inch of water inclusive so as to lift 75% or more of the top layer of the top layer of the bedding via a cushion of air that enables a turbulent airflow to freely distribute the forced airflow throughout a surface area of the bedding surface area, regardless of whether the bedding is smoothly laid or whether the bedding is irregularly bunched up.

14. The bedding climate control apparatus of claim 13, wherein the bedding climate control device includes a thermal element to perform the conditioning of the forced airflow by imparting heating power via the thermal element.

15. A bedding climate control apparatus, comprising: a bedding climate control device configured to operate by:
actuating a blower or a fan to discharge the forced airflow into an air conduit;
conditioning the forced airflow to reach set parameter values;
delivering the conditioned, forced airflow via the air conduit into a space within bedding to inflate same; and
sensing a parameter of the conditioned, forced airflow to provide readings of the sensed parameter; compensating, based on the readings, for changes in the conditioned, forced airflow attributed to backpressure change in the conditioned, forced airflow and to ambient temperature change by further conditioning the conditioned, forced airflow to again reach the set parameter values; wherein the bedding climate control apparatus is configured so that the forced airflow overcomes a pressure drop from passing through the air conduit to reach the space in the bedding and each of the blower or the fan and the air conduit are oversized to exceed respective dimensions necessary to enable delivery of the forced airflow at the set temperature to the space so that the pressure drop is lower than otherwise and the noise level generated is maintained at less than 65 decibels at one meter away.

16. The bedding climate control apparatus of claim 13, further comprising:
an shut-shutoff timer configured to shut off the thermal element and the blower or the fan each in accord with different time intervals from different settings for each.

* * * * *